United States Patent [19]

Breuer et al.

[11] Patent Number: 5,252,577
[45] Date of Patent: Oct. 12, 1993

[54] METHODS OF DESENSITIZING TEETH

[75] Inventors: Miklos M. Breuer, Brookline; Samuel S. Turesky, Chestnut Hill, both of Mass.

[73] Assignee: Gillette Canada, Inc., Kirkland, Canada

[21] Appl. No.: 847,922

[22] Filed: Mar. 6, 1992

[51] Int. Cl.$^5$ .................... A61K 31/515; A61K 6/00; A61K 7/16
[52] U.S. Cl. .................... 514/270; 106/35; 424/49; 424/54; 433/215
[58] Field of Search ............... 514/270, 271; 424/49–58; 106/35; 433/215

[56] References Cited

U.S. PATENT DOCUMENTS

| | | | |
|---|---|---|---|
| 1,921,722 | 8/1933 | Berendes et al. | 514/270 |
| 1,928,346 | 9/1933 | Axelrod | 514/207 |
| 1,984,733 | 12/1934 | Forbing | 514/270 |
| 2,914,443 | 11/1959 | Lynch | 514/270 |
| 3,122,483 | 2/1964 | Rosenthal | 167/93 |
| 3,689,636 | 9/1972 | Svaja | 424/49 |
| 3,772,431 | 11/1973 | Mlkvy et al. | 424/44 |
| 3,839,568 | 10/1974 | Samour et al. | 514/270 |
| 3,863,006 | 1/1975 | Hodosh | 424/49 |
| 3,868,447 | 2/1975 | Kliment | 514/772 X |
| 3,888,976 | 6/1975 | Mlkvy et al. | 424/44 |
| 3,920,837 | 11/1975 | Schmidt-Dunker | 424/49 |
| 3,937,830 | 2/1976 | Samour et al. | 514/270 |
| 4,011,309 | 2/1977 | Lutz | 424/49 |
| 4,134,969 | 1/1979 | Schmidt-Dunker | 424/49 |
| 4,389,393 | 6/1983 | Schor et al. | 514/270 |
| 4,534,839 | 8/1985 | Schaefer | 433/228.1 |
| 4,619,701 | 10/1986 | Angrick | 106/38.23 |
| 4,631,185 | 12/1986 | Kim | 424/49 |
| 4,710,372 | 12/1987 | Scheller | 424/49 |
| 4,751,072 | 6/1988 | Kim | 424/49 |
| 4,873,269 | 10/1989 | Nakazato | 106/35 |
| 4,889,850 | 12/1989 | Thornfeldt | 424/49 |
| 4,892,736 | 1/1990 | Goodson | 424/435 |
| 4,911,922 | 3/1990 | Masuhara et al. | 424/81 |
| 4,919,939 | 4/1990 | Baker | 424/493 |
| 4,978,391 | 12/1990 | Jones | 106/35 |
| 4,990,327 | 2/1991 | Neirinckx | 424/52 |
| 4,992,258 | 2/1991 | Mason | 424/49 |
| 5,000,941 | 3/1991 | Chernack | 424/49 |
| 5,082,653 | 1/1992 | Pan et al. | 424/54 |
| 5,085,850 | 2/1992 | Pan et al. | 424/49 |
| 5,130,412 | 7/1992 | Wellinghoff et al. | 514/270 |
| 5,147,632 | 9/1992 | Pan et al. | 424/54 |

FOREIGN PATENT DOCUMENTS

| | | |
|---|---|---|
| 441317 | 8/1991 | European Pat. Off. . |
| 480785 | 4/1992 | European Pat. Off. . |
| 3923002 | 1/1991 | Fed. Rep. of Germany . |
| 62-175410 | 8/1987 | Japan . |
| 62-175412 | 8/1987 | Japan . |

OTHER PUBLICATIONS

Berman, *J. Peridontol.*, 56:216 (1984).
Brännström, *Oral Surg. Oral Med Oral Pathol., Odontol. Scand.*, 30:291–311 (1972).
Brännström and Astram, *J. Dental Res.*, 43:619 (1964).
Gunji, *Arch Histo, J.*, 45:45–67 (1982).
Garriott et al., *J. Toxicol. Clin. Toxicol.*, 19:987–995 (1982–1983).
Gennaro (ed). *Remington's Pharmaceutical Sciences*, 18th ed. (Mack Publishing Co. 1990), pp. 1063–1064.
Lecointre et al., *J. Int. Med. Res.*, 14:217–222 (1986).
Närhi et al., *Acta. Physiol. Scand.*, 115:173–178 (1982).
Pashley et al., *Endodont. Dent. Traumatol.*, 3:80–82 (1987).
Pleasants et al., *Oral Surg. Oral Med. Oral Pathol.*, 28:163–165 (1969).
Porter, *Brit. Dental J.*, 125:546–548 (1968).
Rey et al., *J. Oral Med.*, 41:66–67 (1986).
Trowbridge, *J. of Endodontics*, 11:489–497 (1985).
Yoshiyama et al., *J. Dent. Res.*, 69 (6):1293–1297 (1990).
Zoryan et al., *Stromatologiia*, 3:71–74 (1975).

*Primary Examiner*—Shep K. Rose
*Attorney, Agent, or Firm*—Fish & Richardson

[57] ABSTRACT

A method of desensitizing a hypersensitive tooth by topically applying to the tooth a composition including an amount of a barbiturate effective to desensitize the tooth. This desensitizing composition may be included in an excipient or in a sustained-release matrix or microbeads that can be incorporated into toothbrushes, dental floss, dentifrices, dental rinses, etc.

5 Claims, 1 Drawing Sheet

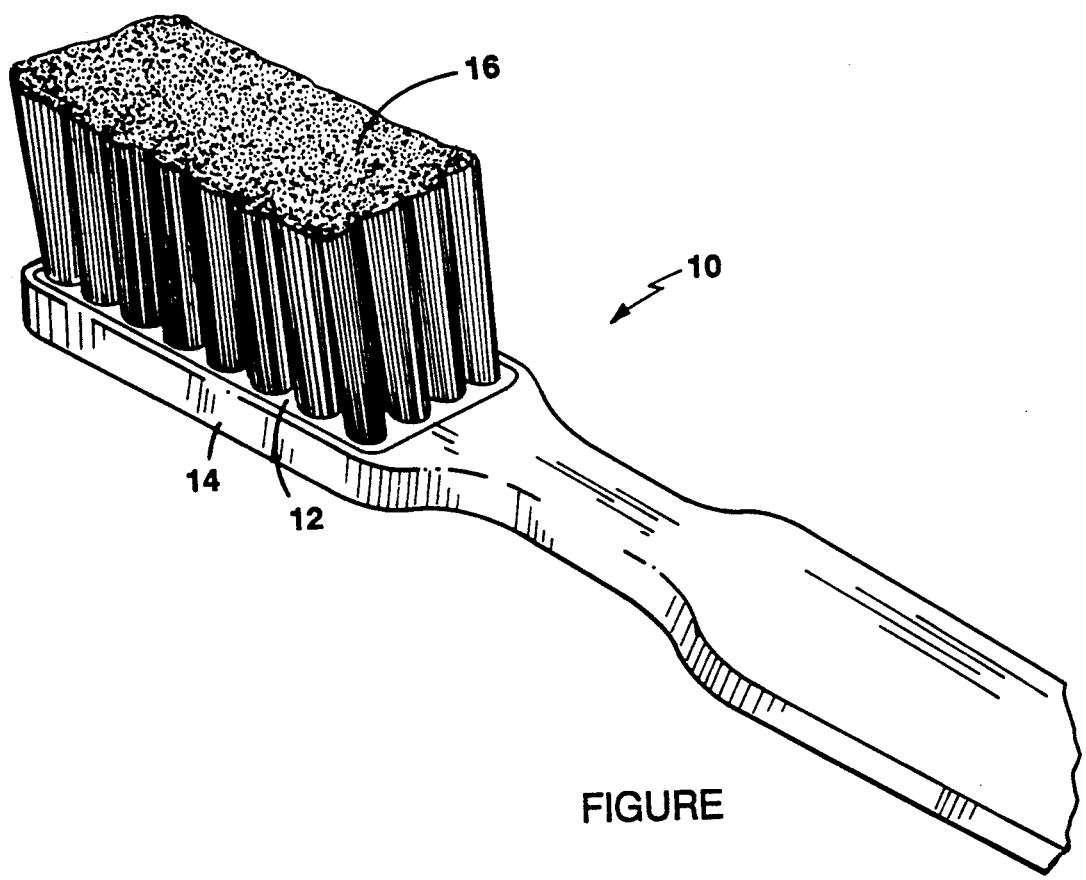
FIGURE

METHODS OF DESENSITIZING TEETH

BACKGROUND OF THE INVENTION

This invention relates to methods of desensitizing teeth.

Radicular dentin exposed by attrition or abrasion of cementum in conjunction with gingival recession or hypereruption of teeth presents a common clinical problem. When the exposed dentin is subjected to thermal, osmotic, electrical, mechanical or dehydrating stimuli, or to certain drugs, the person feels pain, also termed "dentinalgia". In addition, dentinal or cervical hypersensitivity may be experienced by some individuals after tooth root surfaces are exposed by surgical or other periodontal treatments.

The mechanism of dental hypersensitivity is not yet fully understood. The current state of knowledge pertaining to dentinal sensitivity is described in Trowbridge, *J. of Endodontics*, Vol. II, 489 (1985).

According to this review, the following anatomical picture emerges for the innervation of dentin. Nerve fibers enter the tooth through the apical foramina and pass upward in bundles through the radicular pulp. Little branching occurs in the root canal, but upon reaching the coronal pulp, the nerve fibers divide and branch out into the surrounding dentin. When they enter the subodontoblastic region of the pulp, the fibers form an intricate interlacing network known as the plexus of Raschkow. Here the fibers lose their myelin sheath and eventually emerge from their Schwann cell investiture as free nerve endings. Many nerve fibers terminate in the extracellular spaces of the cell-rich zone or the odontoblast layer, whereas others extend the tubules of the predentin or dentin. Gunji, *Arch. Histo. J.* 45:45–67 (1982). Most of these intratubular fibers pass into the predentin or on into the dentin for only a short distance, a few micrometers, although a few fibers penetrate as far as 100 to 150 μm. These intratubular fibers are most numerous in the region of the pulp horns, where it has been estimated that approximately 25% of the tubules contain fibers, whereas only about 15% contain such fibers elsewhere in the coronal dentin. In the root, only about 10% of the tubules contain fibers, which tend to be smaller and do not extend beyond the predentin The precise role of these intratubular fibers in tooth sensitivity is not clear.

According to Trowbridge, supra, the anatomy outlined above makes it difficult to explain the almost instantaneous dentinal pain evoked in response to various stimuli (e.g. cold, heat, air blast, probing, etc.). To account for these findings, investigators have formulated a hydrodynamic hypothesis of stimulus transmission in dentin. This so-called "hydrodynamic theory," as first described in Brännström, *Oral Surg. Oral Med. Oral Pathol., Odontol. Scand.*, 30:291–311 (1972), suggests that minute shifts of dentinal tubule fluid occur in response to tactile, thermal, or osmotic stimuli, and transmit such painful stimuli from the dentin surface to the pulp.

Pulp and dentin sensation is limited to pain, regardless of the stimulus. As noted in Berman, *J. Peridontol.*, 56:216 (1985), there is no direct evidence of the existence of specialized terminal nerve receptors for hot, cold, electrical, osmotic, dehydration, or chemical stimuli in dentin However, movement of dentinal tubule fluid can explain the sensation of pain resulting from such stimuli. For example, dehydration of dentin by dry filter paper elicits pain. This effect can be explained by outward movement of the dentinal fluid into the dehydrating source stimulating the "mechano-receptors" of the odontoblast, with resultant pain. Moreover, Berman, supra, has noted that the coefficient of thermal expansion of the dentinal tubule fluid is about ten times that of the tubule wall Therefore, heat applied to the dentin results in an expansion of the fluid, and, conversely, cold results in a contraction of the fluid, with both creating an excitation of the "mechano-receptors" and therefore, pain.

Trowbridge, supra, has suggested an alternative theory for dentinal pain propagation based on the postulate that odontoblasts can function as pain receptors Odontoblasts extend a considerable distance into the dentinal tubules, and, therefore, do not require a long time period to transmit a pain response after a stimulus is applied to the peripheral dentin Therefore, mechanisms other than fluid movements could account for stimulus propagation However, Brännström and Astram, *J. Dental Res.*, 43:619 (1963), have shown that disruption of the odontoblast layer did not abolish dentin sensitivity, suggesting that odontoblasts do not play an important role in dentinal hypersensitivity.

A number of agents have been investigated for the treatment of hypersensitive teeth They include, e.g., formaldehyde, sodium fluoride, dibasic sodium citrate, sodium monofluorophosphate, sodium silicofluoride, silver nitrate, potassium nitrate, calcium hydroxide, apatite particles, and strontium chloride; usually in a dentifrice base Most of these agents are assumed to act by blocking dentinal tubules and, thus, preventing stimulus propagation from the peripheral dentin to the nerve endings at the pulp-dentin junction through fluid movement.

The Council on Dental Therapeutics of the America Dental Association has recognized "the usefulness and safety" of, or has "accepted," several of such dentifrices containing, e.g., 5% potassium nitrate, 10% strontium chloride, or 1.5% sodium citrate Sodium monofluorophosphate dentifrices have also been shown to reduce the incidence of tooth hypersensitivity. Some of these desensitizing dentifrices include local anesthetics such as benzocaine, lidocaine, etc.

In addition, a variety of agents are used to treat dental pain, such as toothaches, or the pain resulting from dental surgery or tooth extractions For example, quinalbarbitone and meprobamate have been used as systemic pain killers prior to tooth extractions Various anesthetics and analgesics such as benzocaine or lidocaine, benzodiazepines, and drugs such as Dialog, a derivative of barbituric acid and N-acetyl-P-aminophenol, have been used to treat dental pain associated with tooth extractions or dental surgery.

Barbiturates are sedative-hypnotic drugs that act on the central nervous system by depressing the transmission of impulses to the cortex. When used systemically, barbiturates such as barbital and phenobarbital may cause adverse reactions including headaches, myalgia, neuralgia, and arthritic pain. Gennaro (ed.), *Remington's Pharmaceutical Sciences*, 18th ed. (Mack Publishing Co. 1990).

SUMMARY OF THE INVENTION

The present invention is based on the discovery that radicular dentin hypersensitivity is decreased or eliminated by the application of a composition including a small amount of a barbiturate. In a further embodiment, such a solution or composition may include components that precipitate a mineral, e.g., calcium phosphate. Such compositions are applied topically to hypersensitive teeth, e.g., with a cotton swab, dental rinse, tooth brush, or dental floss.

The method of the invention provides a simple, safe, and inexpensive way to treat hypersensitive teeth.

In one embodiment, the invention features a method of desensitizing a hypersensitive tooth by topically applying to the tooth a composition including an amount of a barbiturate effective to desensitize the tooth The barbiturate is preferably sodium barbital and the composition preferably includes a pharmaceutically acceptable excipient An effective amount of the barbiturate may be, e.g., from about 0.01 to about 0.10 molar, and more preferably from about 0.02 to about 0.05 molar.

In another embodiment, the tooth desensitizing composition is topically applied to the tooth from a sustained-release matrix including a support resin, a water-soluble polymer, and desensitizing composition. The support resin is, e g , ethylene vinyl acetate, polyurethane, polyethylene, polystyrene, an ethylene/propylene copolymer, or a styrene/rubber copolymer The water-soluble polymer is e.g., polyethylene oxide, starch, polyvinyl alcohol, a hydroxyalkyl starch, a hydroxyethyl or hydroxypropyl cellulose, or gelatin.

In a further embodiment, the invention features a method of brushing a hypersensitive tooth with an oral brush including a sustained-release matrix to topically apply the barbiturate to the tooth The sustained-release matrix may include between 50 percent and 90 percent by weight ethylene vinyl acetate; between 5 percent and 40 percent by weight polyethylene oxide; and between 1 percent and 30 percent by weight of a 0.0I to about 0.05 M barbiturate composition.

The invention also features a method of desensitizing a hypersensitive tooth wherein the tooth desensitizing composition further includes microparticles, e.g., of polystyrene, that include an amount of the barbiturate effective to desensitize the tooth The microparticles may have an outer surface onto which the barbiturate has been adsorbed. For example, the barbiturate may be ionically charged, e.g., negatively, and the outer surface may be oppositely charged, e.g., positively. Such microparticles may be, for example, between 0.01 $\mu$ and 10 $\mu$ in diameter.

Such desensitizing microparticles may be used in a variety of ways including, flossing the hypersensitive tooth with dental floss coated with the microparticles, brushing with an oral brush including bristles coated with the microparticles, applying a dentifrice including the microparticles to the hypersensitive tooth, and/or rinsing the hypersensitive tooth with an oral rinse including the microparticles.

Without being bound to any theory, it is believed that the barbiturate relieves the radicular dentin sensitivity by stopping peripheral nerve stimulation by way of the odontoblastic processes.

Other features and advantages of the invention will be apparent from the description of the preferred embodiment thereof, and from the claims.

BRIEF DESCRIPTION OF THE DRAWING

The Figure is a schematic of a toothbrush including a polymeric sustained-release matrix.

DESCRIPTION OF THE PREFERRED EMBODIMENTS

Desensitizing Composition

The preferred composition includes an amount of a barbiturate, which is clinically effective to desensitize a tooth, in a pharmaceutically acceptable excipient.

The preferred barbiturate for use in the invention is sodium barbital, 5,5-Diethyl-2,4,6 (1H,3H,5H)-pyrimidinetrione or 5-5-diethylbarbituric acid (Mallinckrodt, Inc., St. Louis, Missouri), which has the chemical formula ($C_8H_{11}N_2NaO_3$), and which may be obtained by the condensation of ethyl diethylmalonate with urea.

Other barbiturates that may be used include amobarbital (Amytal-Lilly), amobarbital sodium (Amytal Sodium-Lilly), butabarbital sodium (Butisol Sodium-Carter Wallace), mephobarbital (Mebaral-Winthrop), pentobarbital (Nembutal-Abbott), pentobarbital sodium (Nembutal Sodium-Abbott), phenobarbital (Luminal), phenobarbital sodium (Luminal Sodium-Winthrop), secobarbital (Seconal-Lilly), secobarbital sodium (Seconal Sodium-Lilly), talbutal (Lotusate-Winthrop), and aprobarbital (Alurate-Roche).

Pharmaceutically acceptable excipients that may be used are inert carriers for the barbiturate active ingredient in the desensitizing composition. Such excipients may be, e.g., liquids, gels, or pastes, such as water, alcohol/water mixtures, or standard dentifrice bases such as described in U.S. Pat. No. 3,538,230 (1970) and Pader, M., "Oral Hygiene Products and Practice," (Marcel Dekker, Inc., New York, 1988), p. 437-8, Tables 2 and 3.

The preferred desensitizing composition is a solution including at least 0.010 to 0.10 M sodium barbital or other barbiturate as the only tooth desensitizing ingredient. More preferably, this solution includes 0.02 to 0.05 M sodium barbital. A mineralizing component may also be included in the composition as an additional tooth desensitizing ingredient. An example of such a solution has the following formulation, see, Strates et al., *J. Phys. Chem.*. 61:279 (1957)(for a 1000 cc of solution):

0.02 M barbital (3.684g in 900 ml boiled $H_2O$);
0.14 M KCl (10.870g added by droplets);
0.0013 M $CaCl_{12}$ (0.1523 g dissolved in 10 cc $H_2O$);
0.0021 M $KH_2PO_4$ (0.3909 g dissolved in 10 cc $H_2O$);
add approx. 10 ml KOH (7.4553 grams in 100 cc $H_2O$);
titrate until pH=7.4; and
add $H_2O$ to reach a total volume of 1000 cc (this solution should be kept cold and stoppered).

This solution has 6.4 mg % of Ca, and 8.9 mg % of P.

Protocol for Testing Treatment of Radicular Dentin Hypersensitivity

Subjects with recessed gingivae and a history of radicular dentin hypersensitivity affecting at least three teeth are selected for the study. To test for pain, each tooth with exposed dentin is isolated with cotton rolls and stimulated by a three-second blast of cold air from an air syringe. As described by M. Addy and R. Newcombe, *Br. Dental J.*, 163:45–51(1987), the subject grades the response for each tooth subjectively as: 0=no discomfort; 1=discomfort, but not severe pain; 2=severe pain during stimulus application; 3=severe pain persisting after stimulation. The sensitive teeth in each subject are recorded, and an equal number of non-sensitive teeth are tested in each subject as a control.

After a minimum five-minute rest period, sites sensitive to cold air are treated with one of the following: (A) an aqueous test solution of 0.02 M sodium barbital, pH 7.6, prepared with distilled, deionized water; (B) a solution of Gel-Kam Dentin Bloc TM 0.4% stannous fluoride gel (Scherer Labs, Dallas, Texas); or (C) a control solution of distilled, deionized water. Three five-second applications are made with a cotton pellet soaked with one of the solutions during a thirty-second period Subjects are permitted to expectorate after the thirty-second period elapses.

After the experimental or control applications are applied, each tooth is subjected to a three-second blast of cold air from an air syringe and sensitivity is scored as described above. After two weeks, the subjects subjectively score improvement for both experimental and control sites as: 0=no improvement; 1=slight improvement; 2=substantial improvement. At that time, sensitivity is again recorded with the three-second cold air blast test. The subjects return after four weeks for a similar assessment.

The examiner and scorer are not aware of the contents of the experimental or control solutions, which are coded for subsequent analysis.

Eighty-five male and female subjects ranging approximately in age from 22 to 80 were treated with the test solution. There was immediate improvement in all -subjects, varying from moderate to complete desensitization. The duration of the desensitization was not determined.

Application From A Sustained-Release Matrix

In a further embodiment, the invention includes applying the desensitizing composition of the invention with a sustained-release matrix made from a support resin, a water-soluble substance (preferably a water-soluble polymer), and the desensitizing composition. When the matrix contacts water, the water-soluble substance dissolves, causing the release of the desensitizing composition. Such a matrix is described in U.S. Ser. No. 07/749,137 by M. Tseng and M. Philbrook, which was filed on Aug. 23, 1991 and is assigned to the same assignee as the present application, and is hereby incorporated by reference.

As shown in the Figure, such a matrix 12 of, e.g., a polymeric material, may be fastened to a toothbrush 10 to apply the composition during brushing The brush preferably includes bristles 16 commonly found in toothbrushes, but also can be designed for massaging the gums rather than the teeth. For example, Kaminski et al., U.S. Ser. No. 07/724,129, which was filed on Jul. 1, 1991 and is assigned to the same assignee as the present application and is hereby incorporated by reference, describes an interdental foam brush in which the brush portion is made of a soft polyurethane foam.

The Figure shows a 2-3 mm. thick polymeric matrix 12 attached to the brush head 14 of a toothbrush 10. The bristles 16 traverse the matrix 12 and are anchored in the brush head in the usual manner. The active material is 6 g sodium barbiturate, incorporated into the polymeric matrix 12, and is released by elution when the brush is wetted. By capillary action of the bristles 16, the active material is transferred to the gingival and dentin surfaces.

Preferred polymers for the support resin of the matrix include polystyrene, polyurethane, ethylene vinyl acetate, polyethylene, styrene/rubber, and ethylene/propylene. The most preferred support resins are ethylene vinyl acetate polymers.

The preferred water-soluble substances are polymers, e.g., starches, polyvinyl alcohols, polyethylene oxides, hydroxyalkyl starches, hydroxyethyl and hydroxypropyl celluloses, and gelatins. The most preferred polymers are polyethylene oxides, most preferably a Polyox ® having a molecular weight of between 100,000 and 5,000,000. The preferred Polyox ® is WSR N-750 (DuPont), which has a molecular weight of 300,000.

In use, such a toothbrush 10 is rinsed with water, toothpaste is applied, and then the head 14 of the brush is inserted into the mouth to brush the teeth. Upon contact with water, some of the desensitizing composition diffuses out of the matrix 12, onto and down the bristles 16, and onto the teeth, desensitizing them. As the water-soluble polymer, e.g., Polyox ®, slowly dissolves with repeated uses of the brush, water is allowed to penetrate into the matrix, making more of the desensitizing composition accessible by diffusion from the matrix core. Eventually, all of the Polyox ® and desensitizing composition have left the matrix, and the toothbrush is discarded.

The matrix 12 is designed to incorporate the desired criteria of release rate, dosage, and effective template lifetime by adjusting the thickness of the template included on the brush, and the quantities of desensitizing composition and water-soluble polymer included in the matrix. The higher the desired dosage, the greater the quantities of water-soluble polymer and desensitizing composition included in the matrix. Also, to increase the released dosage, a more water-soluble form of polymer can be employed. The lifetime of a given matrix also can be increased by increasing the thickness of the matrix.

Application From Microbeads

In another embodiment, the desensitizing composition may be adsorbed onto the surfaces of, or incorporated into, microbeads or microparticles that can be coated onto, e.g., toothbrush bristles or dental floss, or dispersed in dental rinses or dentifrices, and used to apply the composition to the teeth during brushing, flossing, or rinsing. Such microparticles are described in U.S Ser. No. 07/759,535 by J. Spencer, which was filed on Sep. 13, 1991 and is assigned to the same assignee as the present application, and is hereby incorporated by reference.

The particles are released from the toothbrush bristles or dental floss during brushing or flossing and contact the surface of the teeth, clinging to the surface and providing good desensitizing action. In the case of a coated toothbrush, only a portion of the particles are released from the bristles each time brushing occurs. As a result, the toothbrush provides a low dosage of the desensitizing composition over the course of many uses before the supply of microparticles on the bristles has been used up. Moreover, it is believed that the released particles cling to the teeth, slowly releasing the desensitizing composition and desensitizing the teeth even after brushing or flossing is complete.

Such particles are, e.g., polystyrene microspheres having an average diameter of between $0.05\mu$ and $1\mu$, more preferably between $0.3\mu$ and $1\mu$. The most preferred microparticles for use on toothbrush bristles have an average diameter of about $0.86\mu$. Such polystyrene microspheres are available from a number of sources, e.g., Interfacial Dynamics Corp. of Portland, Oregon, packaged as a 5.41 percent w/w suspension in distilled water. Other types of organic polymeric particles that can be used comprise polyvinyltoluene and methacrylate-styrene copolymers.

The general methodology used to produce the preferred polystyrene microspheres is well-known and is described, for example, in Chung-li et al., *Prog. Colloid Poly. Sci.*, 60:163-175 (1976); Goodwin et al., *J. Colloid Poly. Sci.* 252:464 (1974); Goodwin et al., *Brit. Poly. J.*, 5:347 (1973), which are incorporated herein by reference.

In a preferred embodiment, the microparticles have an ionic charge and the desensitizing compositions have an opposite ionic charge. The preferred desensitizing composition is negatively charged, whereas the outer surface of the preferred polystyrene microspheres has a positive charge.

Other Embodiments

Other embodiments are within the following claims.

What is claimed is:

1. A method of desensitizing a hypersensitive tooth comprising topically applying to the tooth a composition comprising an amount of a barbiturate effective to desensitize the hypersensitive tooth.

2. The method of claim 1, wherein said barbiturate is sodium barbital.

3. The method of claim 1, wherein said composition further comprises a pharmaceutically acceptable liquid excipient.

4. The method of claim 1, wherein said effective amount of said barbiturate is from about 0.01 to about 0.10 molar.

5. The method of claim 4, wherein said effective amount of said barbiturate is from about 0.02 to about 0.05 molar.

* * * * *

UNITED STATES PATENT AND TRADEMARK OFFICE
CERTIFICATE OF CORRECTION

Page 1 of 2

PATENT NO. : 5,252,577
DATED : October 12, 1993
INVENTOR(S) : Miklos M. Greuer, et. al.

It is certified that error appears in the above-indentified patent and that said Letters Patent is hereby corrected as shown below:

Title page, item [75], inventors: add Jean L. Spencer, Boston Massachusetts.
[56], add References Cited:
"4,057,621   11/1977   Pashley et al.   424/49"
"4,634,589   1/1987    Scheller         424/49"
"4,867,988   9/1989    Chernack         424/490"
Title page, under Other Publications:
"Rey" should be --Rye--.
Column 1, line 66, after "dentin" insert a period.
Column 2, line 14, after "receptors" insert a period.
Column 2, line 18, after "dentin" insert a period.
Column 2, line 20, after "gation" insert a period.
Column 2, line 26, after "teeth" insert a period.
Column 2, line 41, after "citrate" insert a period.
Column 2, line 48, after "extractions" insert a period.
Column 2, line 50, after "extractions" insert a period.
Column 3, line 12, after "tooth" insert a period.
Column 3, line 15, after "excipient" insert a period.
Column 3, line 22, "eg" should be --e.g.--.
Column 3, line 24, after "copolymer" (second occurrence) insert a period.
Column 3, line 31, after "tooth" insert a period.
Column 3, line 35, "0.0I" should be --0.01--.
Column 3, line 41, after "tooth" insert a period.
Column 4, line 16, after "include" insert a colon.
Column 4, line 46, "$CaCl_{12}$" should be --$CaCl_2$--.
Column 5, line 12, after "period" insert a period.

UNITED STATES PATENT AND TRADEMARK OFFICE
CERTIFICATE OF CORRECTION

PATENT NO. : 5,252,577
DATED : October 12, 1993
INVENTOR(S) : Miklos M. Greuer, et. al.

It is certified that error appears in the above-indentified patent and that said Letters Patent is hereby corrected as shown below:

Column 5, line 49, after "brushing" insert a period.

Signed and Sealed this

Ninth Day of August, 1994

Attest:

BRUCE LEHMAN

Attesting Officer      Commissioner of Patents and Trademarks